United States Patent [19]
Takahashi et al.

[11] Patent Number: 4,824,994
[45] Date of Patent: Apr. 25, 1989

[54] METHOD FOR PRODUCTION OF N-PROTECTED-ALPHA-L-ASPARTYL-L-PHENYLALANINE METHYL ESTER

[75] Inventors: Satoji Takahashi, Yokkaichi; Katsumi Sugiyama, Yokosuka, both of Japan

[73] Assignee: Ajinomoto Co., Inc., Tokyo, Japan

[21] Appl. No.: 650,498

[22] Filed: Sep. 14, 1984

[30] Foreign Application Priority Data

Sep. 30, 1983 [JP] Japan ................... 58-182529

[51] Int. Cl.⁴ .......................................... C07C 101/02
[52] U.S. Cl. ....................................... 560/38; 560/41
[58] Field of Search ..................... 260/112.5 R

[56] References Cited

U.S. PATENT DOCUMENTS

| | | | |
|---|---|---|---|
| 3,492,131 | 1/1970 | Schlatter et al. | 260/112.5 R |
| 3,786,039 | 1/1974 | Ariyoshi et al. | 260/112.5 R |
| 3,879,372 | 4/1975 | Boesten | 260/112.5 R |
| 3,933,781 | 1/1976 | Bachman et al. | 260/112.5 R |
| 3,962,207 | 1/1976 | Uchiyama et al. | 260/112.5 R |
| 4,173,562 | 11/1979 | Bachman et al. | 260/112.5 R |

*Primary Examiner*—Delbert R. Phillips
*Assistant Examiner*—F. T. Moezie
*Attorney, Agent, or Firm*—Oblon, Fisher, Spivak, McClelland & Maier

[57] ABSTRACT

A method for the production of N-carbobenzoxy-α-L-aspartyl-L-phenylalanine methyl ester characterized by the reaction of L-phenylalanine methyl ester with fine N-carbobenzoxy-L-aspartic anhydride crystals, is disclosed.

10 Claims, 1 Drawing Sheet

METHOD FOR PRODUCTION OF N-PROTECTED-ALPHA-L-ASPARTYL-L-PHENYLALANINE METHYL ESTER

DETAILED DESCRIPTION OF THE INVENTION

This invention relates to a method for the production of N-carbobenzoxy-α-L-aspartyl-L-phenylalanine methyl ester by the reaction of L-phenylalanine methyl ester with N-carbobenzoxy-L-aspartic anhydride, which method is characterized by using pulverized or finely divided N-carbobenzoxy-L-aspartic anhydride.

α-L-aspartyl-L-phenylalanine methyl ester (hereinafter referred to as "α-APM" for short) is known as an excellent sweetening agent and various methods for its production have been proposed to the art. One of these methods is known to obtain the α-APM by condensing N-carbobenzoxy-L-aspartic anhydride (hereinafter referred to as "Z-L-Asp anhydride" for short) and L-phenylalanine methyl ester in water or an organic solvent thereby producing N-carbobenzoxy-α-L-aspartyl-L-phenylalanine methyl ester (hereinafter referred to as "Z-α-APM" for short), and subsequently depriving the condensate of the N-protective group thereof.

This method, however, inevitably by-produces N-carbobenzoxy-β-L-aspartyl-L-phenylalanine methyl ester (hereinafter referred to as "Z-β-APM" for short), an isomer of the Z-α-APM. The by-production of the Z-β-APM causes lowering of the yield of the Z-α-APM and consequently the yield of the α-APM, the end product. The by-produced Z-β-APM also implies that the α-APM as the end product is accompanied by β-L-aspartyl-L-phenylalanine methyl ester (hereinafter referred to as "β-APM" for short) as one of impurities. Since the β-APM produces no sweet taste, the α-APM accompanied by the β-APM must be refined by removal of the β-APM. To obtain the α-APM, the end product, in high yield, therefore, it has been extremely important that the formation of the Z-β-APM should be repressed and the formation ratio of the Z-α-APM to the Z-β-APM (hereinafter referred to as α/β ratio) should be heightened.

The inventors continued a diligent study with a view to heightening the α/β ratio and eliminating the disadvantage described above. They have unexpectedly found that when the Z-L-Asp anhydride to be used for the condensation with L-phenylalanine methyl ester is in the form of fine crystals or a suspension thereof, the α/β ratio is notably heightened to an unexpected extent and, consequently, the yield of the α-APM is increased. This knowledge has led to the perfection of this invention.

It is known to the art that the Z-L-Asp anhydride to be used in this method is obtained, for example, by dissolving or suspending N-carbobenzoxy-L-aspartic acid in an organic solvent and allowing a dehydrating agent such as acetic anhydride to react upon the resultant solution or suspension.

The inventors tested the Z-L-Asp anhydride crystals obtained as described above to determine the relation between the particle diameter of the crystals and the α/β ratio.

Dry crystals of the Z-L-Asp anhydride (particle diameter 200 to 300 microns) were obtained by a procedure as indicated in Example 1 hereof, pulverized in a mortar, and classified by sieving into groups of Z-L-Asp anhydride crystals of varying particle diameter ranges.

The Z-L-Asp anhydride crystals of a varying particle diameter range and L-phenylalanine methyl ester were subjected to condensation under the conditions indicated in Example 1. The Z-α-APM and the Z-β-APM formed in the reaction solution were quantitatively analyzed by high-performance liquid chromatography and the α/β ratio was found.

The results which are given in FIG. 1 show that the α/β ratio increased to an unexpectable extent as the particle diameter of the Z-L-Asp anhydride crystals decreased. For example, it is noted from FIG. 1 that compared with the α/β ratio (4.03), taken as 100, obtained by using the Z-L-Asp anhydride crystals not pulverized or finely divided form, the α/β ratio obtained by using the same crystals but in finely divided form was higher falling in the range of 120 to 150.

The smaller the particle diameter of crystals grows, the more the α/β ratio will be heightened. The particle diameter is not more than 130 microns, more desirably not more than 100 microns, and most desirably not more than 50 microns. Despite the statement "not more than 130 microns," inclusion of a small amount (not more than about 10%) of crystals of particle diameters exceeding 130 microns is tolerable. Incidentally, the Z-L-Asp anhydride crystals obtained under the conditions indicated in Example 1, for instance, generally have particle diameters on the order of 150 to 350 microns.

Finely divided Z-L-Asp anhydride crystals are easy to obtain. Various methods are available for pulverization or fine division of the Z-L-Asp anhydride crystals. For example, mechanical methods such as the method of finely comminuting the Z-L-Asp anhydride crystals with a grinder and the method of converting a suspension of the Z-L-Asp anhydride crystals into an emulsion with a homogenizer may be adopted.

Otherwise, physicochemical methods such as the method of selecting the reaction conditions for enabling the reaction to proceed at low temperatures (0° to 40° C., preferably 10° to 35° C., for example) are also adoptable, whereby a slurry of the fine crystals of Z-L-Asp anhydride is formed.

To effect the condensation, the finely divided Z-L-Asp anhydride crystals or a suspension of the finely divided crystals has only to be mixed with a solution containing L-phenylalanine methyl ester. As regards the conditions for the condensation, those normally adopted for the reaction may be used without any hindrance. As the solvent for containing the finely divided Z-L-Asp anhydride crystals or L-phenylalanine methyl ester, any solvent may be used so far as it is not particularly active upon the reactants and the reaction product.

Typical examples of the solvent include ketones such as acetone and methylethyl ketone, ethers such as diethyl ether, tetrahydrofuran, and dioxane, nitriles such as acetonitrile, esters such as ethyl acetate and methyl propionate, carboxylic acids such as formic acid, acetic acid, and propionic acid, halogenated hydrocarbons such as chloroform, dichloromethane, and ethylene dichloride, hydrocarbons such as toluene, xylene, hexane, and cyclohexane, amides such as dimethyl formamide, dimethyl sulfoxide, γ-butyrolactone, nitromethane, and water. It is permissible to use a mixed solvent consisting of any two or more members selected from the group of solvents just mentioned.

The mol ratio of the Z-L-Asp anhydride and L-phenylalanine methyl ester is in the range of 0.8 to 1.2 and the reaction temperature, for the purpose of repressing racemization of the reaction product to the fullest extent, is kept at or below 100° C., preferably at or below 80° C.

This invention is highly advantageous from the commercial point of view because it permits an increase of the α/β ratio and an increase of the yield of Z-α-APM, notably improves the yield of the α-APM, the end product, and further brings about an effect of repressing the by-production of Z-β-APM.

Figure 1:
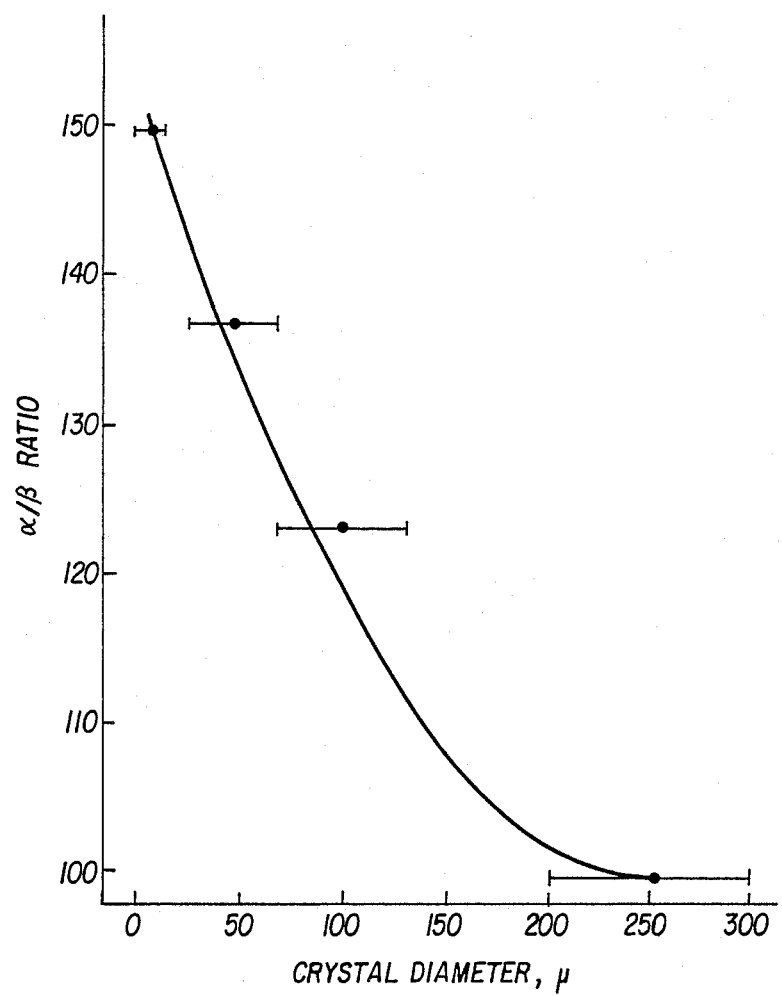
FIG. 1 shows the relation between the particle diameter (in microns) of the Z-L-Asp anhydride (horizontal axis of graph) and the Z-α-APM/Z-β-APM ratio (vertical axis). The values of the α/β ratio are those calculated relative to the α/β ratio (4.03), taken as 100, which was obtained by subjecting undivided Z-L-Asp anhydride crystals (200 to 300 microns) to condensation (by following the procedure of Example 1).

Now, the method of this invention will be described more specifically below with reference to working examples. The amounts of Z-α-APM and Z-β-APM indicated in the working examples are those determined by quantitative analysis by the use of high-performance liquid chromatography (model LC-3A of Shimadzu, filler-Unicil QC-18 of Gas Chro Industry).

EXAMPLE 1

Under agitation, 100 g (0.374 mol) of N-carbobenzoxy-L-aspartic acid, 41.4 g (0.405 mol) of acetic anhydride, and 100 g of toluene were mixed at 55° C. for five hours to undergo a dehydrating reaction, whereby Z-L-Asp anhydride is formed. The resultant reaction mixture was filtered to collect the formed Z-L-Asp anhydride. The Z-L-Asp anhydride crystals were washed with toluene and dried to afford 86.3 g (0.346 mol) of Z-L-Asp anhydride crystals.

A 50-g portion of the crystals was finely divided in a mortar to particle diameters of 0.1 to 20 microns. The particle diameters were measured with the aid of a microscope.

A 10-g portion of the finely divided Z-L-Asp anhydride crystals was suspended in 20 g of toluene and 5 g of acetic acid. The resultant suspension was, after mixed with 100 g of toluene solution cooled to 5° C. and containing 8.6 g (0.048 mol) of L-phenylalanine methyl ester, stirred at room temperature for one hour.

The resultant condensate, by quantitative analysis, was found to contain 14.6 g (0.0341 mol) of Z-α-APM and 2.5 g (0.00584 mol) of Z-β-APM, indicating that the α/β ratio was 5.84.

EXAMPLE 2

A 10-g portion (0.04 mol) of the finely divided Z-L-Asp anhydride crystals obtained in Example 1 was, after mixed with 100 g of toluene solution cooled to 5° C. and containing 8.6 g (0.048 mol) of L-phenylalanine methyl ester and 5 g of acetic acid, stirred at room temperature for one hour.

The resultant reaction solution was found, by quantitative analysis, to contain 14.5 g (0.0338 mol) of Z-α-APM and 2.5 g (0.00584 mol) of Z-β-APM, indicating that the α/β ratio was 5.80.

EXAMPLE 3

Sixty g (0.225 mol) of N-carbobenzoxy-L-aspartic acid, 24.8 g (0.243 mol) of acetic anhydride, and 120 g of toluene were stirred at 55° C. for three hours to undergo a hydrating reaction.

The resultant reaction solution was wholly treated in a homogenizer for 15 minutes to comminute the Z-L-Asp anhydride crystals in the reaction solution. A small fraction of crystals was observed under a microscope to find that these crystals had particle diameters in the range of 0.05 to 15 microns.

The reaction solution containing the finely divided crystals was wholly combined under stirring with 600 g of toluene solution cooled to 5° C. and containing 41.4 g (0.231 mol) of L-phenylalanine methyl ester to induce condensation.

Quantitative analysis of a 2-g portion of the resultant condensation reaction solution showed that the solution contained 82.3 g (0.192 mol) of Z-α-APM and 13.6 g (0.0317 mol) of Z-β-APM, indicating that the α/β ratio was 6.05.

The condensation reaction solution was added with 1200 g of water and the mixture was heated to 60° C. The resultant solution was further mixed with 1.5 g of 2% palladium-carbon. Hydrogen gas was blown into the mixture at a rate of 400 ml per minute for one hour. The resultant reaction solution was filtered and separated into a toluene layer and a water layer. The water layer was cooled and left standing overnight at 5° C. The crystals which had been precipitated were separated by filtration, washed with 60 ml of cold water, and dried. Consequently, there was obtained 46.2 g (0.157 mol) of α-APM.

COMPARATIVE EXPERIMENT 1

The entire amount of the reaction solution obtained by the anhydride formation reaction was subjected to the procedure of Example 4, except that the treatment with a homogenizer was omitted.

A small fraction of the anhydride formation reaction solution was observed under a microscope to find that Z-L-Asp anhydride crystals of particle diameters of 150 to 250 microns accounted for more than 90% of all the crystals contained therein.

The condensation reaction solution, by quantitative analysis, was found to contain 76.5 g (0.179 mol) of Z-α-APM and 18.8 g (0.0439 mol) of Z-β-APM, indicating that the α/β ratio was 4.07. The amount of the α-APM consequently produced was 38.9 g (0.132 mol).

EXAMPLE 4

Sixty g (0.225 mol) of N-carbobenzoxy-L-aspartic acid, 24.8 g (0.243 mol) of acetic anhydride, and 120 g of toluene were mixed and stirred at 28° C. for 24 hours to induce a reaction. A small portion of Z-L-Asp anhydride crystals in the resultant reaction solution was observed under a microscope to find that crystals of particle diameters of 20 to 80 microns accounted for more than 80% of all the crystals contained therein.

The entire amount of the anhydride formation reaction solution was combined, while under stirring, with 600 g of toluene solution containing 41.4 g (0.231 mol) of L-phenylalanine methyl ester kept cooled to 5° C., to undergo condensation reaction.

Quantitative analysis of a 2-g portion of the condensation reaction solution showed that the solution contained 80.5 g (0.188 mol) of Z-α-APM and 15.5 g (0.0362 mol) of Z-β-APM, indicating that the α/β ratio was 5.19.

The condensation reaction solution was mixed with 1200 g of water and heated to 60° C. The resultant solution was further added with 2.0 g of 2% palladium-carbon. Hydrogen gas was blown into the mixture under stirring at a rate of 400 ml per minute for 1.5 hours.

The reaction mixture was filtered and separated into a toluene layer and a water layer. Then, the water layer was cooled and left standing overnight at 5° C. The crystals precipitated in the solution were separated by filtration, washed with 60 ml of cold water at 3° C., and to afford 45.6 g (0.155 mol) of α-APM.

What is claimed is:

1. A method for the production of N-carbobenzoxy-α-L-aspartyl-L-phenylalanine methyl ester, which comprises:
   obtaining crystals of N-carbobenzoxy-L-aspartic anhydride wherein at least about 90% of said crystals have a particle diameter of not more than 130 μm;
   reacting said crystals with L-phenylalanine methyl ester; and
   isolating N-carbobenzoxy-α-L-aspartyl-L-phenylalanine methyl ester.

2. The method of claim 1, wherein said crystals are obtained by pulverizing dry crystals of N-carbobenzoxy-L-aspartic anhydride crystals.

3. The method of claim 1, wherein said crystals are obtained by converting a suspension of N-carbobenzoxy-L-aspartic anhydride crystals into an emulsion.

4. The method of claim 1, wherein said crystals are obtained by a reacting N-carbobenzoxy-L-aspartic acid with acetic anhydride at a temperature of from 0° to 40° C.

5. The method of claim 4, wherein said temperature is from 10° to 35° C.

6. The method of claim 1, wherein at least about 90% of said crystals have a particle diameter of not more than 100 microns.

7. The method of claim 1, wherein at least about 90% of said crystals have a particle diameter of not more than 50 microns.

8. The method of claim 1, wherein said reaction is conducted at or below 100° C.

9. The method of claim 1, wherein said reaction is conducted at or below 80° C.

10. A method for the production of α-aspartyl-L-phenylalanine methyl ester, which comprises:
    obtaining crystals of N-carbobenzoxy-L-aspartic anhydride wherein at least about 90% of said crystals have a particle diameter of not more than 130 μm;
    reacting said crystals with L-phenylalanine methyl ester to produce N-carbobenzoxy α-L-aspartyl-L-phenylalanine methyl ester;
    removing the carbobenzoxy group from the N-carbobenzoxy-α-L-aspartyl-L-phenylalanine methyl ester; and
    isolating α-L-aspartyl-L-phenylalanine methyl ester.

* * * * *